United States Patent
Harma (10) Patent No.: US 10,156,558 B2
(45) Date of Patent: Dec. 18, 2018

(54) DETECTION AND QUANTIFICATION OF POLYMERIC ANALYTES USING FLUORESCENT LANTHANIDE DETECTION NOT RELYING ON CHARGE TRANSFER FROM POLYMER AROMATIC GROUPS

(71) Applicant: AQSENS OY, Espoo (FI)

(72) Inventor: Harri Harma, Turku (FI)

(73) Assignee: KEMIRA OYJ, Helsinki (FI)

( * ) Notice: Subject to any disclaimer, the term of this patent is extended or adjusted under 35 U.S.C. 154(b) by 0 days.

(21) Appl. No.: 15/036,845

(22) PCT Filed: Sep. 24, 2014

(86) PCT No.: PCT/FI2014/050725
§ 371 (c)(1),
(2) Date: May 16, 2016

(87) PCT Pub. No.: WO2015/075299
PCT Pub. Date: May 28, 2015

(65) Prior Publication Data
US 2016/0274079 A1 Sep. 22, 2016

(30) Foreign Application Priority Data
Nov. 19, 2013 (FI) .................................. 20130343

(51) Int. Cl.
| | | |
|---|---|---|
| G01N 33/44 | (2006.01) | |
| G01N 21/64 | (2006.01) | |
| G01N 33/542 | (2006.01) | |
| G01N 33/58 | (2006.01) | |

(52) U.S. Cl.
CPC ......... G01N 33/442 (2013.01); G01N 21/643 (2013.01); G01N 21/6408 (2013.01); G01N 33/542 (2013.01); G01N 33/582 (2013.01); G01N 2021/6439 (2013.01)

(58) Field of Classification Search
CPC .. G01N 33/542; G01N 33/582; G01N 33/442; G01N 21/6408; G01N 21/643; G01N 2021/6439
See application file for complete search history.

(56) References Cited

U.S. PATENT DOCUMENTS

| | | | | |
|---|---|---|---|---|
| 4,058,732 A * | 11/1977 | Wieder | ............... | G01N 21/6408 250/461.1 |
| 5,876,960 A | 3/1999 | Rosen | | |
| 2011/0111388 A1 | 5/2011 | Hennig et al. | | |
| 2013/0171623 A1 | 7/2013 | He | | |
| 2013/0171624 A1 | 7/2013 | He | | |

FOREIGN PATENT DOCUMENTS

| | | |
|---|---|---|
| JP | 2000271564 | 10/2000 |
| WO | 9638724 | 12/1996 |
| WO | 2011088193 | 7/2011 |
| WO | 2015075299 | 5/2015 |

OTHER PUBLICATIONS

Gilles Muller: "Luminescent chiral lanthanide(iii) complexes as potential molecular probes", Dalton Transactions, No. 44, Jan. 1, 2009, pp. 9692-9707, XP055159688.
Bünzli et al.: "Taking advantage of luminescent lanthanide ions", Chemical Society Reviews, Chemical Society, London, GB, vol. 34, No. 12, Dec. 1, 2005, pp. 1048-1077, XP002593476.
Karhunen et al., "Luminescence Switching by Hybridization-Directed Mixed Lanthanide Complex Formation", Analytical Chemistry, American Chemical Society, US, vol. 82, No. 2, Jan. 15, 2010, pp. 751-754, XP002593475.
Karhunen et al., "Quantitative detection of well-based DNA array using switchable lanthanide luminescence", Analytica Chimica Acta, Elsevier, Amsterdam, NL, vol. 772, Feb. 28, 2013, pp. 87-92, XP028526740.
Bekiari et al., "Intensely Luminescent Materials Obtained by Combining Lanthanide Ions, 2,2'-Bipyridine, and Poly (ethyleneglycol) in Various Fluid or Solid Environments", Chemistry of Materials, American Chemical Society, US, vol. 11, No. 11, Nov. 1, 1999, pp. 3189-3195, XP000866820.
Lehmusvuori et al., "High-performance closed-tube PCR based on switchable luminescence probes", Analytica Chimica Acta, Elsevier, Amsterdam, NL, vol. 731, Apr. 20, 2012, pp. 88-92, XP028509845.
Finnish Search Report dated Jun. 19, 2014; Application No. 20130343.
J. Georges, "Lanthanide-sensitized Luminescence and Applications to the Determination of Organic Analytes", Analyst, 1993, vol. 118, pp. 1481-1486.
Kogej et al., "Understanding the Interaction between Trivalent Lanthanide Ions and Stereoregular Polymethacrylates through Luminescence, Binding Isotherms, NMR, and Interaction with Cetylpyridinium Chloride", Langmuir, Nov. 2013, vol. 29, No. 47, pp. 14429-14437.
Zhang et al., "Time-Resolved Probes Based on Guanine/Thymine-Rich DNA-Sensitized Luminescence of Terbium (III)", Analytical Chemistry, Dec. 2013, vol. 85, No. 23, pp. 11665-11674.
International Preliminary Report on Patentability PCT/FI2014/050725 dated Dec. 7, 2015.
Hovinen et al., "Bioconjugation with Stable Luminescent Lanthanide (III) Chelates Comprising Pyridine Subunits", Bioconjugate Chem., 2009, vol. 20, No. 3, pp. 404-421.
Lipchik et al., "Time-Resolved Luminescence Detection of Spleen Tyrosine Kinase Activity through Terbium Sensitization", Analytical Chemistry, 2013, 85, pp. 2582-2588.

* cited by examiner

Primary Examiner — Christopher Adam Hixson
(74) Attorney, Agent, or Firm — Young & Thompson (57) ABSTRACT

A method for determining samples including one or more organic polymers by mixing them with lanthanide(III) ions and detecting the signal of the lanthanide(III) ion chelated with the organic polymer.

13 Claims, 5 Drawing Sheets

Figure 10

DETECTION AND QUANTIFICATION OF POLYMERIC ANALYTES USING FLUORESCENT LANTHANIDE DETECTION NOT RELYING ON CHARGE TRANSFER FROM POLYMER AROMATIC GROUPS

FIELD

This invention relates to a method for measuring concentration of one or more organic polymers in a sample with the aid of lanthanide(III) ions.

BACKGROUND

Because of their unique luminescence properties lanthanide(III) chelates are often used as non-radioactive markers in a wide variety of routine and research applications. For example, U.S. Pat. No. 4,565,670 discloses a heterogeneous method for fluorescence spectroscopic determination of a biologically active substance wherein a lanthanide ion is dissociated from EDTA-labeled immune reactant at low pH-value in solution containing a suitable detergent, a synergistic compound and a β-diketone to amplify the fluorescence after the separation.

Luminescent stable lanthanide(III) chelates has extended the use of time resolution to homogeneous assays. For example, EP 0324 323A discloses an immunochemical assay including a luminescent lanthanide(III) chelate covalently bound to an immune reactant and one or more fluorescence modulating substances such as proteins and detergents.

In the assays described above the detection is based on time-resolved fluorometric analysis of signal derived from a lanthanide(III) chelate including one or more aromatic structures, which absorb the excitation energy and transfer it to the lanthanide(III) ion, and chelating groups such as β-diketones and carboxylic acids. Also tyrosine and phosphotyrosine residues of peptides and proteins are known to sensitize terbium luminescence. These methods relate to the use of a known concentration of peptide residues added to the sample at known concentration. The change in the peptide modification is followed and at the know concentration of enzyme and its activity/binding inhibitors and enhancers. In other words, all concentrations of all molecules in the reaction are known.

US 2011/0111388 discloses a method of detection of an analyte containing polyamino acid and other macromolecules in the aid of luminescent markers that are coupled to the analyte after chemical activation.

U.S. Pat. No. 6,329,205 discloses staining of amine-containing polymers using photoluminescent complexes of europium(III).

The aromatic structures exhibiting the properties described above are also known in art as antennas.

It is known that lanthanide(III) ions can be detected also in the in the absence of antenna molecules. Bekiari et al. have shown that association of lanthanide ions with the ether oxygens of the ethylene glycol groups of PEG chains results in increasing their luminescence intensity in several fluid environments (Chem. Mater. 1999, 11, 3189-3195). The document teaches that such a concentration dependency is achieved for low molecular-weight non-ionic PEG-200 and PEG-400 when measured in the presence of relatively high concentration of lanthanide ion (40 mM) and using time-resolved luminescence detection method. The lowest detectable concentration was approximately 10% (by weight) solution for PEG-200 corresponding to a 0.5 M solution.

SUMMARY

The present invention is based on the observation that examining organic polymers including two or more chelating groups can be performed simply by mixing them with lanthanide(III) ions and detecting the signal of the lanthanide(III) ion chelated with the organic polymers.

According to one aspect, the present technology concerns a method for measuring concentration of one or more organic polymers in a sample the method including:
admixing the sample and lanthanide(III) ion, wherein the total concentration of the organic molecules in the sample is below 0.5 M and the concentration of the lanthanide(III) ion is 10 mM, exemplary between about 10 mM and about 0.001 mM,
detecting signal derived from the lanthanide(III) ion with time-gated luminescence measurement, and
measuring the quantity of one or more organic polymers in the sample based on the signal derived from the lanthanide(III) ion, wherein the organic polymer includes two or more groups capable of chelating with the lanthanide(III) ion and are selected from carboxylates, sulfonates, carboxamides, phosphates, phosphonates and amines, in proviso that the polymer is not protein or oligopeptide.

According to another aspect the present technology concerns a computer program product including computer executable instructions for controlling a programmable processor to examine a sample wherein the program is adapted to evaluate the data obtainable by a method.

According to another aspect the present technology concerns a computer program product comprising computer readable medium encoded with a computer program.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

DESCRIPTION

The organic polymer measured according to the present technology includes two or more chelating groups selected from carboxylates, sulfonates, phosphates, phosphonates and amines. Accordingly, the chelating groups are the following:

carboxylate ($COO^-$), sulfonate ($—SO_3^-$)

carboxamide ($—CONH—$, $—NHCO—$, $—CONH_2$)

phosphate wherein R is alkyl
phosphonate wherein R is alkyl and
amine

These groups are able to chelate with a lanthanide(III) ion. The net charge of the organic polymer may change as a function of pH, and can be negative, positive and neutral. The organic polymer can also be zwitterionic.

As defined herein the term chelating group include ionizing groups. According to a preferable embodiment the chelating groups are negatively charged.

As defined herein a lanthanide chelate is a chemical compound in a form of a heterocyclic ring containing a lanthanide ion attached by coordinate bonds to at least two non-metal ions.

As defined herein the organic polymer includes two or more ionizable/chelating groups, preferably at least three ionizable/chelating groups, more preferably more than four ionizable/chelating groups and most preferably more than 12 ionizable/chelating groups capable of chelating with the lanthanide(III) ion, i.e. to form a lanthanide chelate. The groups are selected from carboxylates, sulfonates, phosphates, carboxamides and amines. According to a preferable embodiment, the groups are selected from carboxylates, sulfonates, phosphates, and amines.

As defined herein, a polymer is a chemical compound or mixture of compounds consisting of repeating structural units created through a process of polymerization.

The organic polymer to be detected according to the present technology does not need to contain aromatic groups that are able to chelate with the lanthanide ion and absorb excitation energy and transfer it essentially to lanthanide(III) ion, i.e. to act as an antenna group. The antenna group has to have sufficient energy transfer properties and it has to be in close proximity to the chelated lanthanide(III) ion. Exemplary antenna groups have been disclosed in Bioconjugate Chem., 2009, 20 (3), pp 404-421, incorporated here as a reference.

According to one embodiment, the organic polymer to be analyzed according to the present technology does not include an aromatic group wherein there are less than three bonds between the aromatic group and at least one of the two or more chelating/ionizable groups.

According to one embodiment the organic polymer measured according to the present technology does not include any aromatic groups.

As defined herein, the concentration of the organic polymer in the sample is unknown. Prior art knows methods where the concentration of molecules in a reaction is known but the sample molecule may take two or more forms e.g. by phosphorylation/dephosphorylation on enzyme activity. In the context of this invention, the concentration of the organic polymer is unknown and adaptation of two or more forms is not considered to be a sample of an unknown origin.

The lanthanide ion used in the present technology is selected from europium, terbium, samarium and dysprosium, preferably europium and terbium, even more preferably europium. A combination of lanthanide ions may be used according to the invention.

The lanthanide ion used in the present technology is in the form of lanthanide salt, such as lanthanide(III) chloride or lanthanide(III) acetate. A preferable lanthanide(III) salt is lanthanide(III) halide, such as europium(III) chloride. Accordingly, the lanthanide(III) ion is introduced as a salt, such as europium chloride and the lanthanide(III) chelate is formed upon conjugation of the lanthanide(III) ion with the sample.

The organic molecule is polymeric. According to one embodiment the its molecular weight is over 400 g/mol. Exemplary polymeric chelating molecules are DNA, polystyrene sulfonates and polyethylene imines. When charged, the organic polymer can be anionic, cationic and zwitterionic.

Figure 1:
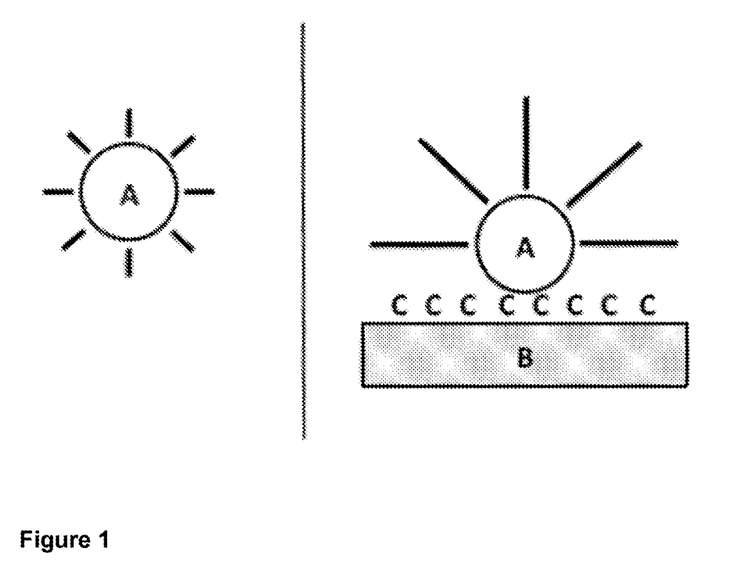
FIG. 1 illustrates an exemplary schematic the principle of the present technology. A lanthanide ion (A) alone gives no or low level of luminescence signal (left). Admixing the lanthanide ion with an organic polymer (B) containing chelating groups (C) such as carboxylates, sulfonates, phosphates, phosphonates and/or amines, high luminescence signal is measured (right). The signal is correlated to the concentration of the sample.

FIG. 1 illustrates the principle of the method of the present technology. The time-resolved signal derived from the lanthanide(III) ion, such as $Eu^{3+}$ is increased in the presence of charged molecules such as charged organic polymers. This observation has been utilized in the measuring the presence and/or quantity of one or more organic polymers in the sample.

Figure 2:
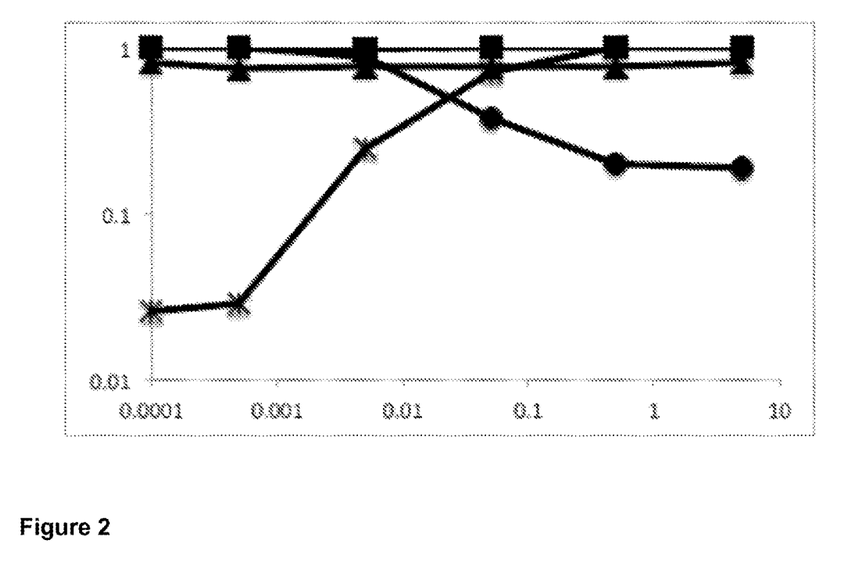
FIG. 2 illustrates measurement of circle: polystyrene sulfonate; triangle: PEG 400; square: PEG 6000; and star: polyethylene imine. Luminescence signal of $Eu^{3+}$ was monitored at the excitation wavelength of 340 nm and emission wavelength of 615 and 1 mM of $EuCl_3$ in $H_2O$. X-axis: concentration of different compounds (weight-%); Y-axis: time-resolved luminescence signal (counts).

FIG. 2 illustrates an exemplary embodiment of the present technology. Different compounds were measured in the presence of 1 mM $Eu^{3+}$. All data were monitored at the excitation wavelength of 340 nm and emission wavelength of 615 nm, and the europium signal was detected as a function of the concentration of the organic molecule. It is clearly seen that the europium signal is dependent on the concentration of anionic (grey square; polystyrene sulfonate), and cationic (star; polyethylene imine) organic polymers. In strict contrast, the europium signal does not change as a function of non-charged organic molecules.

Figure 3:
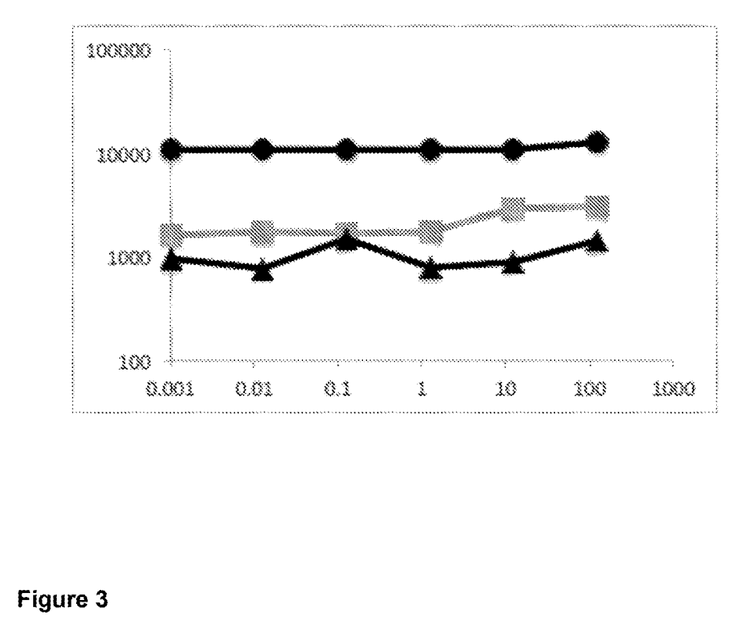
FIG. 3 illustrates measurement of PEG 400 in the presence of three different $Eu^{3+}$ concentrations. Luminescence signal of $Eu^{3+}$ was monitored at the excitation wavelength of 340 nm and emission wavelength of 615 nm. Circle: $EuCl_3$ 10 mM; Grey square: $EuCl_3$ 1 mM; and triangle: $EuCl_3$ 0.10 mM. X-axis PEG 400 concentration (mM); Y-axis: time-resolved luminescence signal (counts).
Figure 4:
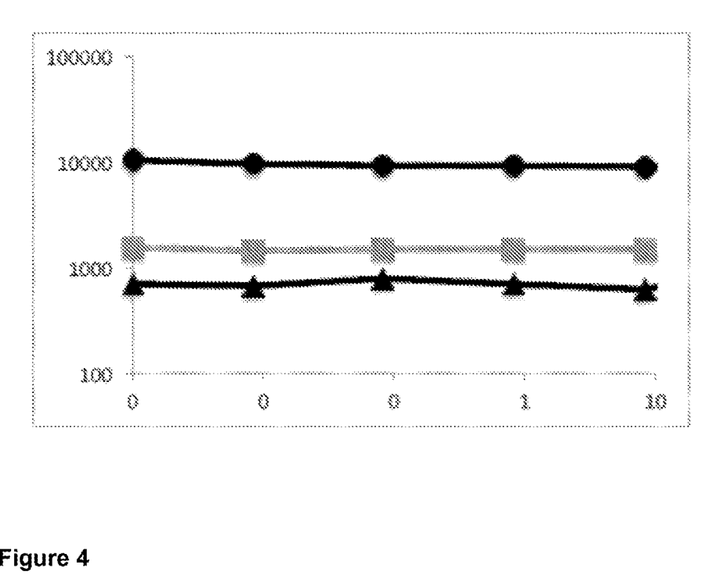
FIG. 4 illustrates measurement of PEG 6000 in the presence of three different $Eu^{3+}$ concentrations. Luminescence signal of $Eu^{3+}$ was monitored at the excitation wavelength of 340 nm and emission wavelength of 615 nm. Circle: $EuCl_3$ 10 mM; Grey square: $EuCl_3$ 1 mM; and triangle: $EuCl_3$ 0.10 mM. X-axis PEG 6000 concentration (mM); Y-axis: time-resolved luminescence signal (counts).

FIGS. 3 and 4 illustrate comparative examples wherein two non-charged organic polymers (PEG 400 and PEG 6000) were measured in the presence of three different concentrations of $Eu^{3+}$. All data were monitored at the excitation wavelength of 340 nm and emission wavelength of 615 nm. It is clearly seen that in both cases the europium signal does not change as a function of the concentration of $Eu^{3+}$.

Figure 5:
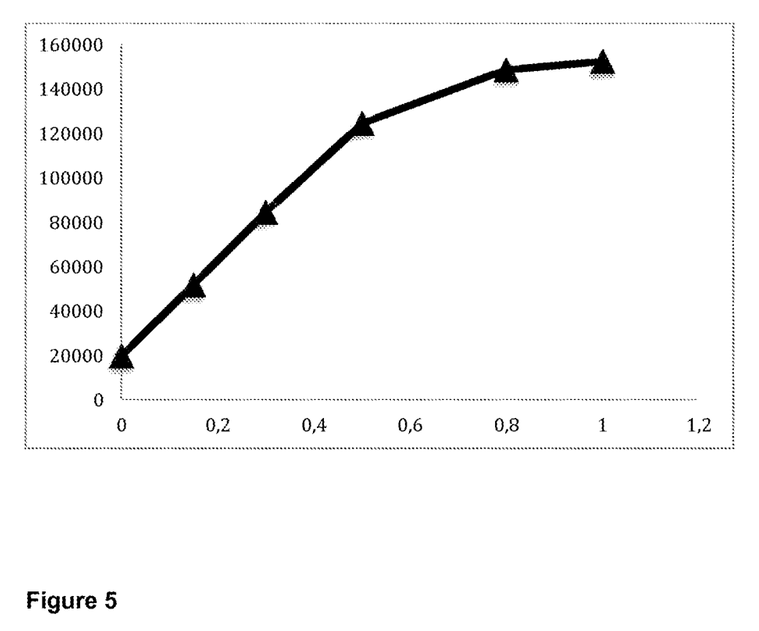
FIG. 5 illustrates measurement of a sulfonated co-polymer in presence of $EuCl_3$ (0.0001 mM) and HEPES (5 mM). Luminescence signal from $Eu^{3+}$ was monitored at excitation wavelength of 240 nm and emission wavelength of 615 nm. X-axis: concentration (ppm); Y-axis: time-resolved luminescence signal (counts).
Figure 6:
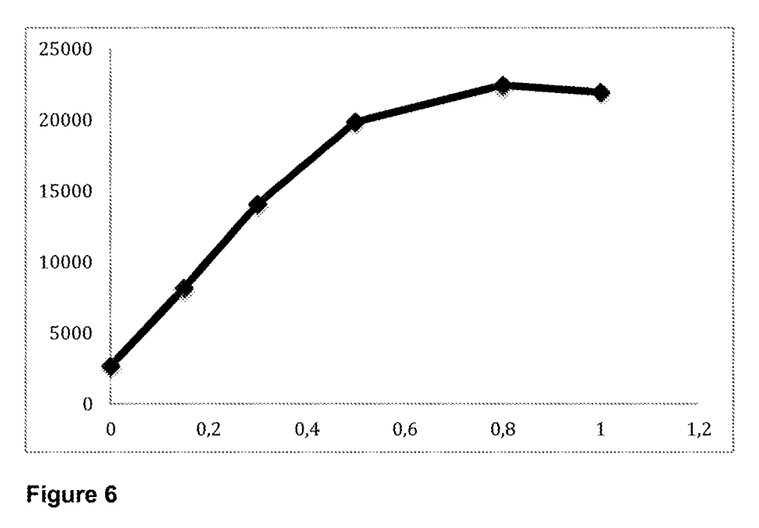
FIG. 6 illustrates measurement of another sulfonated co-polymer in presence of $EuCl_3$ (0.0001 mM) and HEPES (5 mM). Luminescence signal from $Eu^{3+}$ was monitored at excitation wavelength of 395 nm and emission wavelength of 615 nm. X-axis: concentration (ppm). Y-axis: time-resolved luminescence signal (counts).
Figure 7:
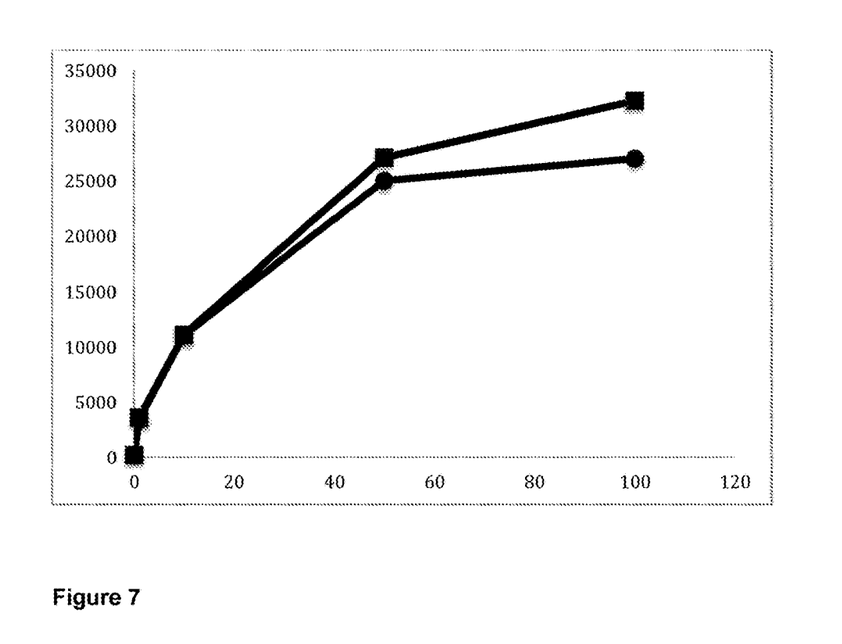
FIG. 7 illustrates measurement of a sulfonated co-polymer (square) and a sulfonated co-polymer with a phosphorous moiety (circle) in presence of $EuCl_3$ (0.01 mM) and HEPES (5 mM). Luminescence signal from $Eu^{3+}$ was monitored at excitation wavelength of 395 nm and emission wavelength of 615 nm. X-axis: concentration (ppm); Y-axis: time-resolved luminescence signal (counts).

The present technology has several advantages. Detection of low sample concentration is often preferred. Prior art teaches that 10% by weight solution (corresponding to 0.5 M solution) of non-ionic polyethylene glycol can be detected, but by using a significant amount of lanthanide ions. As disclosed herein, significant reduction of the detection limit and the concentration of the lanthanide ions can be achieved when the sample substance is ionic. As shown here even by using 10 mM solution of lanthanide ion no polyethylene glycol dependent luminescence signal can be detected even at 0.5 M concentration level for polyethylene glycol 400 or 6000. By contrast, charged organic polymers such as polystyrene sulfonate and polyethylene imine give substrate dependent europium signal over a wide concentration range even in the presence of small amounts of lanthanide(III) ion i.e. 1 mM-0.01 mM (FIGS. 7-10), and even as low as 0.0001 mM (FIGS. 5 and 6).

It is known that at high concentration of polymeric sample substance and lanthanide ion readily precipitate. Thus the concentration of the sample substance and the lanthanide ion must be low enough to achieve an optically sufficiently clear solution for measurement. According to the method disclosed herein, the lanthanide ion concentration must be below about 10 mM, preferably between about 10 mM and about 0.0001 mM, or about 10 mM and about 0.001 mM more preferably between about 1 mM and about 0.01 mM, even more preferably between about 0.1 mM and 0.01 mM and most preferably around 0.01 mM. The concentration of the organic polymer in the sample must be below 10% by weight. If initial concentration of organic polymer in the sample is over 10% by weight, the sample should be diluted. Exemplary diluent is water or aqueous buffer solution.

The method of invention is non-specific. Non-specificity should be understood that no specific binders such as high-affinity ($>1 \cdot 10^7$ $M^{-1}$) antibodies are used and the interaction of the lanthanide ion with the sample has no pre-determined binding site. Other ions such as cations may bind to the sample as the sample has no pre-determined binding property with the lanthanide ion.

The analysis of the organic molecule according to the method of the present technology is performed in a detection vessel. The vessel may be e.g. a well, a part of a fluidic device or a cuvette.

In some applications, the sample includes molecules that have to be removed or diluted prior to analysis. According to this embodiment the sample is subjected to pretreatment step prior to admixing with the lanthanide(III) ion. Exemplary pretreatment methods are size exclusion chromatography, filtration and dilution with an appropriate solution. It should be understood that the pretreatment step means preferably removal or dilution of molecules that may disturb the examination of charged molecules of interest, not isolation of the charged organic polymer e.g. by chromatography.

The method described above can be used for measuring the quantity of the organic polymers in the sample. If the sample substance is known, the method allows the quantification of the charged organic polymer in the sample. It also allows the quantification of total amount of charged organic polymers in the sample.

The analysis of the organic molecule according to the method of the present technology can be quantitative. For quantitive analysis, typically a standard curve or standard point is first prepared and then the concentration of the known sample substance is calculated using the standard curve or the standard point. Alternatively the instrument has been pre-calibrated to support the quantification.

According to an embodiment the present technology, the lanthanide(III) ion is detected using two or more time-gated luminescence wavelengths. The two or more wavelengths relates to two or more excitation or two or more emission wavelengths. In an example, the lanthanide(III) ion is detected using two excitation wavelengths and one emission wavelength. In another example, two excitation wavelengths and two emission wavelengths is used to detect the lanthanide(III) ion. Preferably, two or more excitation wavelengths and one emission wavelength is used.

According to another embodiment the present technology includes a computer program including software modules for determining information indicative for the sample, in order to evaluate the signal derived from the method. The software modules can be e.g. subroutines of functions implemented with a suitable programming language and with a complier suitable for the programming language and the programmable processor.

A computer program product according to an exemplifying embodiment of the present technology includes a computer readable medium e.g. a compact disc, encoded with a computer program according to an embodiment of the present technology.

A signal according to the exemplary embodiment is encoded to carry information defining a computer program according the embodiment.

EXAMPLES

Example 1. Measurement of Polymers with $Eu^{3+}$.
An Exemplary Procedure

The assays disclosed in FIGS. 5 and 6 were performed by preparing assay buffer stock by adding 100 µl 500 mM HEPES-NaOH, pH 7.4 and 10 µl of 10 µM $EuCl_3$ to 800 µl of deionized water. 25 µl of assay buffer was placed to wells of black microtiter plates and 225 µl of sample in brine was added on top. Luminescence signal from $Eu^{3+}$ was monitored at excitation wavelength of 240 nm and 395 (experiments disclosed in FIGS. 5 and 6, respectively), and emission wavelength of 615 nm with TECAN M1000 spectrofluorometer (Tecan, Mannedorf, Austria).

Figure 8:
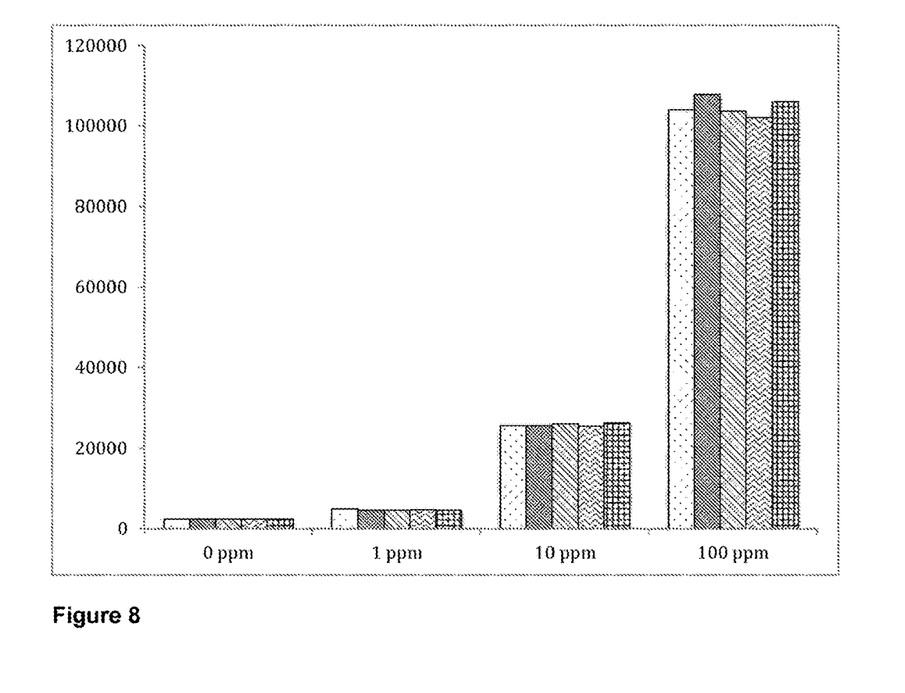
FIG. 8 illustrates measurement of a sulfonated co-polymer (dotted) and s sulfonated co-polymer with fluorescent moiety (gray) and determination of total concentration of two polymers in various ratios. The ratios used are given as untagged:tagged: 1:1 (diagonal lines); 9:1 (zigzag) and 1:9 (grid). The measurements were made in presence of $EuCl_3$ (0.01 mM) and HEPES (5 mM). Luminescence signal from $Eu^{3+}$ was monitored at excitation wavelength of 395 nm and emission wavelength of 615 nm. X-axis: total concentration of polymer in sample (ppm); Y-axis: time-resolved luminescence signal (counts).
Figure 9:
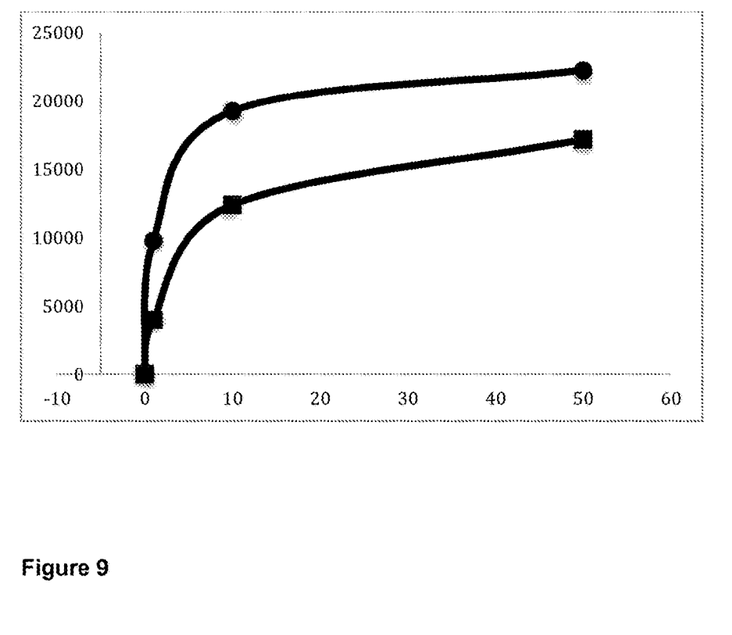
FIG. 9 illustrates measurement of a polyacrylic acid (square) and a polymaleic acid (circle) in presence of $EuCl_3$ (0.01 mM) and HEPES (5 mM). Luminescence signal from $Eu^{3+}$ was monitored at excitation wavelength of 240 nm and emission wavelength of 615 nm. X-axis: concentration (ppm); Y-axis: time-resolved luminescence signal (counts).

Example 2. Measurement of Multiple Polymers and Determination Total Concentration of Polymers Total concentration of polymers mixed in various ratios was determined by adding 2.5 ml of sample in brine (NaCl 35.03 g/l, $CaCl_2.2H_2O$ 2.24 g/l, $MgCl_2.6H_2O$ 1.46 g/l, KCl 0.21 g/l and $BaCl_2.2H_2O$) to a PS cuvette containing 25 µl 500 mM HEPES-NaOH pH 7.4 and 25 µl of 1 mM $EuCl_3$. After mixing the luminescence signal from $Eu^{3+}$ was monitored at excitation wavelength of 395 nm and emission wavelength of 615 nm with a spectrofluorometer (Aqsens, Espoo, Finland). The results are shown in FIG. 8.

Example 3. Measurement of Concentration of Polymers in the Produced Water Samples Two sets of standard samples containing 0, 10, 20 50 and 100 ppm standards were prepared by spiking salt solution (NaCl 35.03 g/l, $CaCl_2.2H_2O$ 2.24 g/l, $MgCl_2.6H_2O$ 1.46 g/l, KCl 0.21 g/l and $BaCl_2.2H_2O$) with polymer. The first set of standards contained untagged polymer. Second set of the standards contained polymer with fluorescent moiety. The samples containing the two polymers in mixture were prepared by spiking produced water obtained from an oil filed in the North Sea.

Concentration of polymers in the produced water samples:

| Matrix | Fluorescent moiety concentration (ppm) | Untagged concentration (ppm) | Total concentration (ppm) |
| --- | --- | --- | --- |
| Produced water | 0 | 0 | 0 |
| Produced water | 1 | 9 | 10 |
| Produced water | 1 | 19 | 20 |
| Produced water | 30 | 20 | 50 |
| Produced water | 80 | 20 | 100 |

The samples and standards were pretreated with gelfiltration columns (Illustra NAP-25, GE life-science, USA). The columns were equilibrated with 20 ml of the salt solution before adding the sample. A sample collection tube was placed under the columns and 2.5 ml of sample was added to the column followed by 3 ml of brine to elute the polymer from column. Total of 5.5 ml of sample was collected.

Figure 10:
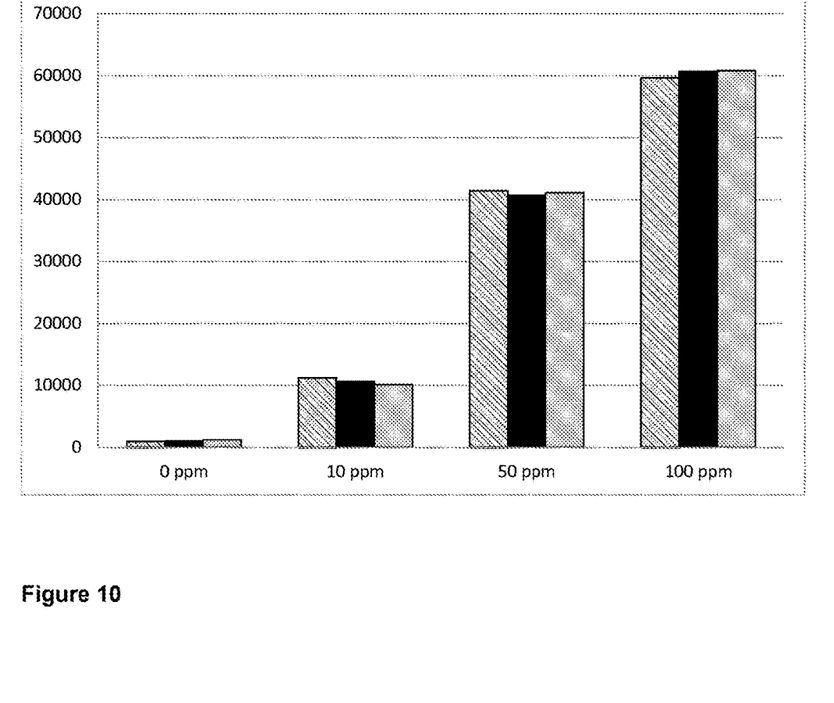
FIG. 10 illustrates measurement of a sulfonated co-polymer (diagonal lines) and s sulfonated co-polymer with fluorescent moiety (black) and measurement of these two polymers in mixture (gray) in North Sea produced water. Y-axis photon counts, X-axis total polymer concentration in the sample.

The measurement was carried out by adding 2.5 ml of pre-treated sample or standard to a PS cuvette containing 25 µl 500 mM HEPES-NaOH pH 7.4 and 25 µl of 1 mM $EuCl_3$. After mixing the luminescence signal from $Eu^{3+}$ was monitored at excitation wavelength of 395 nm and emission wavelength of 615 nm with a spectrofluorometer (Aqsens, Espoo, Finland). The results are shown in FIG. 10.

Example 4. Analysis Sulfonated Co-Polymer and Sulfonated Co-Polymer with a Phosphorous Moiety The assay was performed by preparing assay buffer stock by adding 100 µl 500 mM HEPES-NaOH pH 7.4 and 10 µl 100 µM $EuCl_3$ to 800 µl of deionized water. 25 µl of assay buffer was placed on bottom of black microtiter plates and 225 µl of sample in brine was added on top.

Example 5. Measurement of Concentration of Polyacrylic Acid and Polymaleic Acid

The assay was performed by preparing assay buffer stock by adding 100 µl 500 mM HEPES-NaOH pH 7.4 and 10 µl 100 µM $EuCl_3$ to 800 µl of deionized water. 25 µl of assay buffer was placed on bottom of black microtiter plates and 225 µl of sample in brine was added on top.

The specific examples provided in the description given above should not be construed as limiting the scope and/or the applicability of the appended claims.

The invention claimed is:

1. A method for measuring concentration of one or more kinds of organic polymers in a sample, the method comprising:
   admixing the sample and lanthanide(III) ion in the form of lanthanide salt, wherein the total concentration of the organic polymers in the sample is below 0.5 M and the concentration of the lanthanide(III) ion is ≤10 mM,
   detecting a signal derived from the lanthanide(III) ion with a time-gated luminescence measurement, and
   measuring a quantity of the one or more kinds of organic polymers in the sample based on the signal derived from the lanthanide(III) ion, wherein each kind of organic polymer comprises two or more groups capable of chelating with the lanthanide(III) ion and are selected from the group consisting of carboxylates, sulfonates, phosphates, phosphonates, carboxamides and amines, in proviso that the polymer is not a protein or an oligopeptide.

2. The method according to claim 1, wherein the concentration of the lanthanide(III) ion is from 0.001 mM to 10 mM.

3. The method according to claim 1, wherein the lanthanide(III) ion is admixed as lanthanide(III) halide.

4. The method according to claim 3, wherein the lanthanide(III) halide is selected from europium(III) chloride and terbium(III) chloride.

5. The method according to claim 3, wherein the lanthanide(III) halide is europium(III) chloride.

6. The method according to claim 1, wherein at least one of the kinds of organic polymers does not comprise an aromatic group that is able to absorb excitation energy and transfer it essentially to the lanthanide(III) ion.

7. The method according to claim 1, comprising introducing the sample through a pretreatment system prior to admixing with the lanthanide(III) ion.

8. The method according to claim 7 wherein the system is selected from dilution, filtration and size exclusion chromatography.

9. The method according to claim 1, wherein each kind of organic polymer has a molecular weight >400 g/mol.

10. The method according to claim 1, wherein the sample comprises two or more kinds of organic polymers and one of the organic polymers is quantified.

11. The method according to claim 1, wherein the sample comprises two or more kinds of organic polymers and two or more of the organic polymers are quantified.

12. The method according to claim 1, wherein the sample comprises two or more kinds of organic polymers and the total amount of the organic polymers are quantified.

13. The method according to claim 1, wherein the lanthanide(III) ion is detected using two or more time-gated luminescence wavelengths.

* * * * *